US006871684B2

(12) United States Patent
Engelbart et al.

(10) Patent No.: US 6,871,684 B2
(45) Date of Patent: Mar. 29, 2005

(54) SYSTEM FOR IDENTIFYING DEFECTS IN A COMPOSITE STRUCTURE

(75) Inventors: Roger W. Engelbart, St. Louis, MO (US); Craig Walters, Wentzville, MO (US)

(73) Assignee: The Boeing Company, Seattle, WA (US)

( * ) Notice: Subject to any disclaimer, the term of this patent is extended or adjusted under 35 U.S.C. 154(b) by 30 days.

(21) Appl. No.: 10/217,805

(22) Filed: Aug. 13, 2002

(65) Prior Publication Data

US 2004/0031567 A1 Feb. 19, 2004

(51) Int. Cl.$^7$ .............................................. B32B 31/20
(52) U.S. Cl. ..................... 156/361; 156/378; 156/379; 356/324; 356/300; 356/237.2
(58) Field of Search ................. 156/378, 379, 156/166–174, 176–181, 184–195, 350, 352, 358, 367; 356/300, 324, 237.2

(56) References Cited

U.S. PATENT DOCUMENTS

| | | |
|---|---|---|
| 3,243,509 A | 3/1966 | Stut |
| 4,064,534 A | 12/1977 | Chen et al. |
| 4,120,402 A | 10/1978 | Swanson |
| 4,135,204 A | 1/1979 | Davis, Jr. et al. |
| 4,437,115 A | 3/1984 | Yoshida |
| 4,445,185 A | 4/1984 | Davis, Jr. et al. |
| 4,760,444 A | 7/1988 | Nielson et al. |
| 5,007,096 A | 4/1991 | Yoshida |
| 5,016,099 A | 5/1991 | Bongardt et al. |
| 5,058,174 A | 10/1991 | Carroll |
| 5,058,497 A | 10/1991 | Bishop et al. |
| 5,066,352 A * | 11/1991 | Albers et al. ............... 156/265 |
| 5,187,573 A | 2/1993 | Yoshida |
| 5,237,407 A | 8/1993 | Crezee et al. |
| 5,253,302 A | 10/1993 | Massen |
| 5,258,917 A | 11/1993 | Bruder et al. |
| 5,263,094 A | 11/1993 | Laitinen et al. |
| 5,290,386 A * | 3/1994 | Trudeau ..................... 156/350 |
| 5,331,312 A | 7/1994 | Kudoh |
| 5,333,208 A | 7/1994 | Massen |
| 5,426,509 A | 6/1995 | Peplinski |

(List continued on next page.)

FOREIGN PATENT DOCUMENTS

JP 2001012930 1/2001

OTHER PUBLICATIONS

Richard Sharp, Scott Holmes, Cindy Woodall; M*aterial Selection/Fabrication Issues for Thermoplastic Fiber Placement; Journal of Thermoplastic Composite Materials*; Jan. 1995; pp. 2–13; vol.8; Techtronic Publishing Co., Inc.

(List continued on next page.)

*Primary Examiner*—Chris Fiorilla
*Assistant Examiner*—George Koch
(74) *Attorney, Agent, or Firm*—Alston & Bird LLP

(57) ABSTRACT

The present invention provides an improved system for identifying defects in a composite structure by providing a light source such that defects, and in particular dark defects on a dark background and/or light defects on a light background, can be identified by capturing images of the illuminated composite structure. In particular, the improved system for identifying defects in a composite structure may provide a reflective surface, dispersion elements, and multiple and/or moveable light source(s) and/or camera(s) in order to ensure that the most accurate images of any area of the composite structure, even curved or contoured areas, are captured and processed. As a result, the system of the present invention permits the operator to quickly identify and correct defects which would otherwise create structural flaws or inconsistencies that may affect the integrity of the composite structure.

42 Claims, 7 Drawing Sheets

U.S. PATENT DOCUMENTS

| | | |
|---|---|---|
| 5,440,650 A | 8/1995 | Hieda et al. |
| 5,452,370 A | 9/1995 | Nagata |
| 5,486,819 A | 1/1996 | Horie |
| 5,533,628 A | 7/1996 | Tao |
| 5,562,788 A | 10/1996 | Kitson et al. |
| 5,646,682 A | 7/1997 | Sogabe et al. |
| 5,652,432 A | 7/1997 | Yaginuma |
| 5,700,337 A | 12/1997 | Jacobs et al. |
| 5,751,910 A * | 5/1998 | Bryant et al. ............... 706/2 |
| 5,777,809 A * | 7/1998 | Yamamoto et al. ......... 359/869 |
| 5,963,660 A | 10/1999 | Koontz et al. |
| 6,064,429 A | 5/2000 | Belk et al. |

OTHER PUBLICATIONS

Matthew M. Thomas, Robert A. Giowasky, Bruce E. McIlroy, Todd A. Story; *Manufacturing of Smart Structures Using Fiber Placement Manufacturing Processes*; SPIE; pp. 266–273; vol. 2447.

W. Augustus Elliott, Reed Hannebaum; *Fiber Placement Inspection System An Experimental Approach; 43$^{rd}$ International SAMPE Symposium*; 1998; pp. 957–963; Reed Hannebaum Engineering Services, Published by Society for the Advancement of Material and Process Engineering.

*Infrared Imaging Techniques for Flaw Detection in Composite Materials*, R. Paulson et al., Lockheed Missiles and Space Company, Inc., Sunnyvale, CA, pp. 88–95, undated.

* cited by examiner

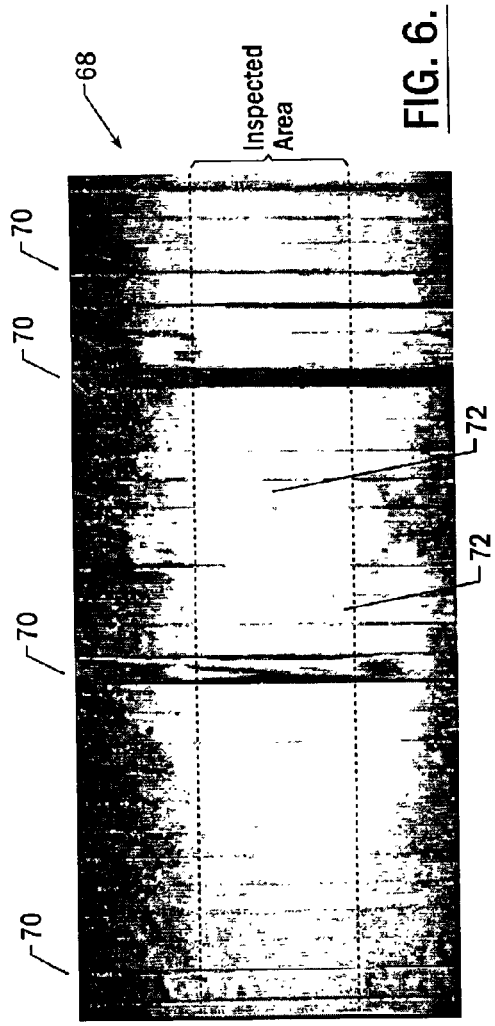
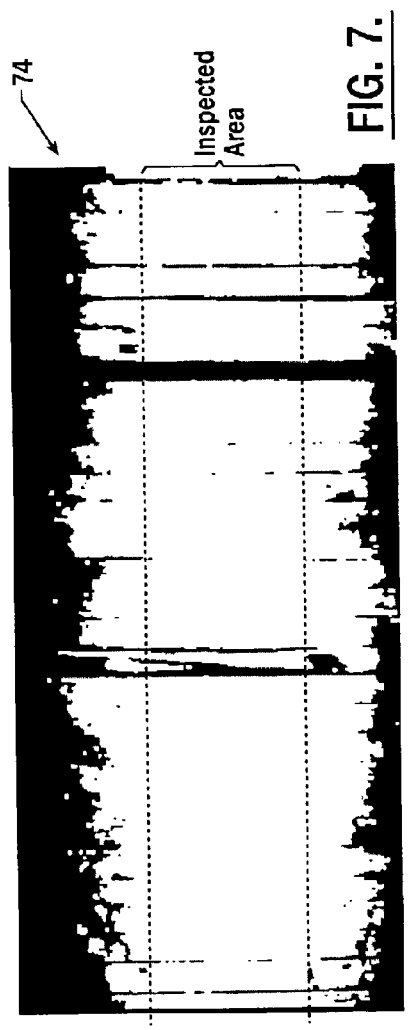

SYSTEM FOR IDENTIFYING DEFECTS IN A COMPOSITE STRUCTURE

BACKGROUND OF THE INVENTION

The present invention relates generally to the fabrication of composite structures, and more particularly to systems and methods adapted for locating defects during fabrication of composite structures.

Composite structures have been known in the art for many years. Although composite structures can be formed in many different manners, one advantageous technique for forming composite structures is a fiber placement or automated collation process. According to conventional automated collation techniques, one or more ribbons of composite material (also known as composite tows) are laid down on a substrate. The substrate may be a tool or mandrel, but, more conventionally, is formed of one or more underlying layers of composite material that have been previously laid down and compacted. In this regard, conventional fiber placement processes utilize a heat source to assist in compaction of the plies of composite material at a localized nip point. In particular, the ribbon or tow of composite material and the underlying substrate are heated at the nip point to increase the tack of the resin of the plies while being subjected to compressive forces to ensure adhesion to the substrate. For example, the plies of composite material can be compacted by a compliant pressure roller as described by U.S. Pat. No. 5,058,497, which is incorporated herein by reference. To complete the part, additional strips of composite material can be applied in a side-by-side manner to form layers and can be subjected to localized heat and pressure during the consolidation process. Other conventional fiber placement process methods are described in U.S. Pat. No. 5,700,337, which is incorporated herein by reference.

Composite laminates that are fabricated by the fiber placement process are typically subjected to a 100% ply-by-ply visual inspection for such defects as tow gaps, overlaps and twists. Typically, the inspection is performed manually by either an inspector or the fiber placement machine operator. The machine must be stopped and the process of laying materials halted until the inspection is complete. During the inspection, the operator verifies the dimensions of any suspect anomalies and quantifies the number of anomalies per given unit area. The anomalies are repaired as needed and laying of the next ply proceeds. However, the fabrication process has been disadvantageously slowed by the inspection process.

To overcome the disadvantages of manually inspecting a workpiece, machine inspection systems have employed video and other images that are processed by a computer to detect the existence of irregularities on an inspected object. For example, U.S. Pat. No. 4,760,444 discloses a machine visual inspection device having video inspection stations for determining the reflectance of different portions of a workpiece. A central processing unit then digitizes the reflectance values and stores the digitized values in memory. The computer also contains a standard image previously stored in memory that serves as a reference to the reflectance values. As such, the computer can compare the standard image to the digitized reflectance values to locate any anomalies. However, this system provides only a single reference point when inspecting workpieces that cannot be modified by the operator.

Another inspection system is disclosed by U.S. Pat. No. 4,064,534, which discloses a television camera and logic circuitry to electronically compare the profile of an image of a workpiece against a standard image whereby the item being inspected or measured can either be rejected or accepted. More specifically, a video image of the workpiece is captured by a TV camera and converted into digital form for recording in a memory device. The recorded image is then compared against a standard image that is preloaded into memory. Based on the differences between the images, a processor determines whether the workpiece passes or fails. However, this system also requires that the standard measurements are preloaded into the computer and not controllable by the operator thereafter.

Yet another conventional inspection system employs a laser that is swept across a workpiece to identify locations on the workpiece where laser reflectivity changes. For example, a gap or other inconsistency would cause a change in the reflectivity of the surface. The reflectivity changes are then interpreted by a computer to identify defects.

Each of these systems, however, is susceptible to obtaining false readings due to glare or other problems caused by ambient lighting or by the laser-based scanning system. In particular, the systems do not provide accurate identification of defects in the contoured/curved regions of workpieces. In this regard, conventional machine-based inspection systems lack suitable lighting to provide the high contrast that is necessary to locate defects on all areas of the workpiece, while preventing ambient lighting and material reflectivity from hampering the identification of defects. The lack of suitable light is especially problematic when inspecting contoured/curved surfaces because the portion of the surface that contours/curves away from the light source cannot be adequately illuminated, and, therefore, identification of defects in the contoured/curved surface is not possible. This inspection process is further complicated during inspection of carbon materials by the appearance of black defects on a black background. In addition, conventional machine-based inspection systems do not readily permit controlled alteration of the definition of defects or the viewing area. Instead, conventional machine-based inspection systems typically have a predefined definition of defects and a presized viewing area that is undesirable during the inspection process.

BRIEF SUMMARY OF THE INVENTION

The systems for identifying defects in a composite structure of the present invention are capable of identifying defects in all areas of a workpiece, even the contoured/curved regions of the workpiece, by more adequately illuminating the surface of the workpiece. In this regard, the system provides ample light and disperses the light over a sufficiently large area of the workpiece such that all of the surfaces of the workpiece, including the contoured/curved surfaces that face away from the light, are adequately illuminated in order to obtain a complete inspection for defects. In addition, the systems of the present invention permit controlled alteration of the viewing area and the ability to view the composite structure as close to the structure as possible, which results in the system accurately identifying the defects in the workpiece. This invention, therefore, saves time, labor and money that would otherwise be necessary to perform a manual inspection of the areas where accurate identifications could not be obtained.

One embodiment of the system for identifying defects in a composite structure during fabrication of the composite structure according to the present invention includes a light source, a reflective surface, and a camera. The light source is positioned relative to the composite structure and illuminates the composite structure. The light generated by the light source reflects differently off of the defects in the composite structure than from the defect free portions of the structure. The light source may be halogen light. In addition, the light source may be moveable relative to the composite structure, and there may be multiple light sources located at different respective positions relative to the composite structure, in order to provide sufficient illumination of the composite structure. The reflective surface is located near the composite structure and is directed toward the illuminated portion of the composite structure. The reflective surface may be a mirror. In addition, there may be multiple reflective surfaces that cooperate to direct an image of the illuminated area of the composite structure to the camera.

The camera is directed toward the reflective surface and receives reflected images of the illuminated portion of the composite structure. Thus, the camera may be positioned further from the illuminated portion of the composite structure than the reflective surface, thereby permitting images of the composite structure to be captured even in instances in which the camera could not be located near the composite structure. The camera may be an infrared-sensitive camera or a visible light camera with infrared-pass filtration, and the camera may be moveable relative to the composite structure. In addition, there may be multiple cameras located at different respective positions relative to the composite structure in order to view the composite structure from an optimal position.

Another embodiment of the present invention includes a light source and a camera as described above, and a dispersion element. The dispersion element is located near the light source and scatters the light generated by the light source over the composite structure, thereby providing more even illumination of the composite structure. The dispersion element may have a stepped configuration to more evenly scatter the light over the composite structure. The dispersion element may be at least partially curved toward the light source, such as by having a parabolic shape with stepped configuration. In addition, the dispersion element may be adjustable in order to direct the scattered light toward a predetermined portion of the composite structure from which the camera receives images.

A further embodiment of the present invention includes a light source and a camera, as described above, where the light source or the camera or both are moveable relative to the composite structure. As such, the light source and/or the camera can be repositioned as appropriate for differently shaped composite structures.

The composite structure may be made of multiple composite strips that are laid down by an automated collation process in which the composite strips are provided by a head unit and compacted to the underlying composite structure by a compaction roller. In this configuration, the reflective surface and the light source are near the compaction roller. In some embodiments, the reflective surface and light source may be mounted on the head unit. In embodiments that include a dispersion element, the dispersion element and the light source may be mounted on the head unit.

The system of the present invention also may include a marking device to mark the composite structure when a defect is identified. Furthermore, a processor for processing the images and outputting a response identifying a defect based upon the images also may be included in the system.

As a result of the light source and camera configurations, the systems of the present invention are capable of viewing and identifying defects in a composite structure, regardless of where the defect is located on the workpiece. Moreover, the utilization of a dispersion element and/or a reflective surface in the systems of the present invention provide additional illumination and viewing capabilities that enable accurate identification of defects in a workpiece, even in areas of the structure that conventional systems cannot reach.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 6 is a graphical view of a computer readout for identifying defects in a composite structure according to one embodiment of the present invention;

FIG. 7 is a graphical view of a binarized image of the graphical view of FIG. 6;

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
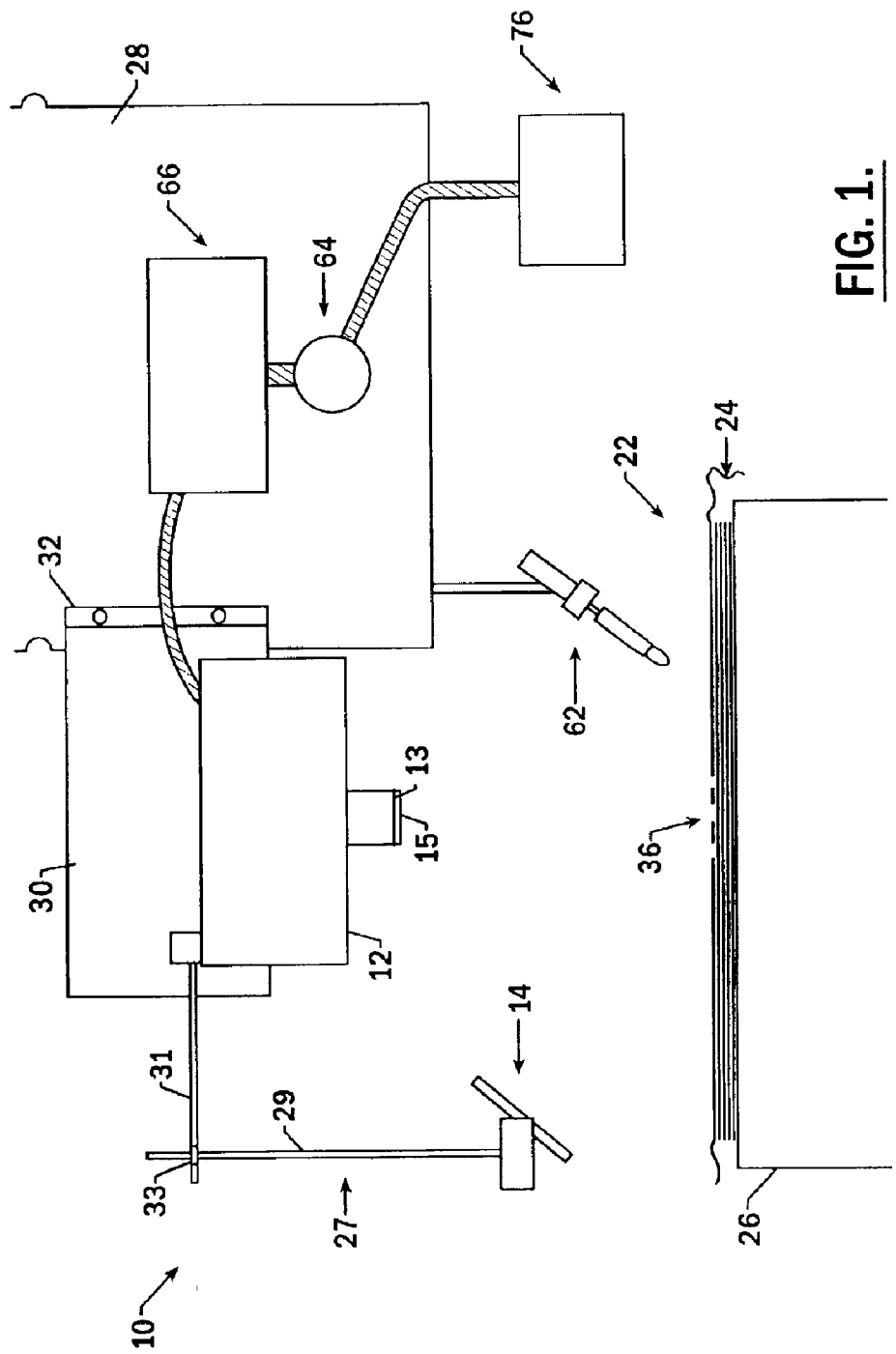
FIG. 1 is a schematic view of a system for identifying defects in a composite structure during fabrication thereof according to one embodiment of the present invention.
Figure 2:
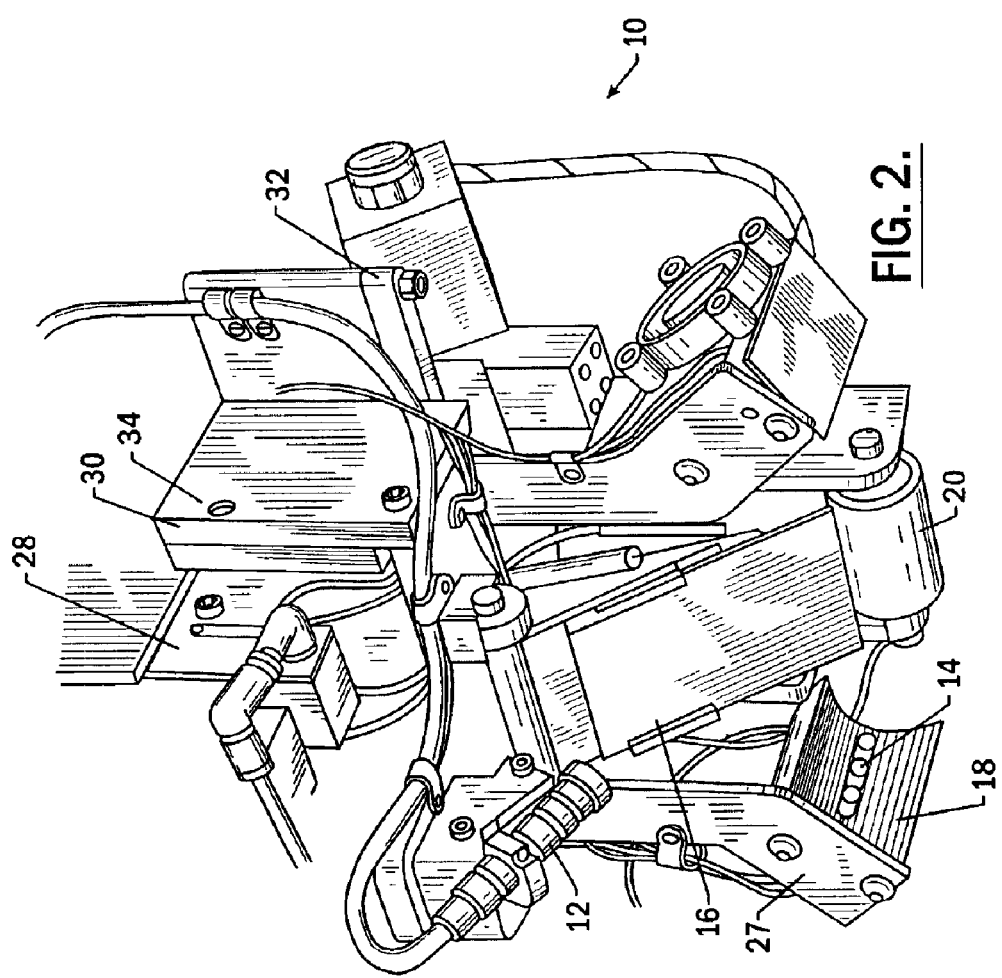
FIG. 2 is an alternative embodiment of a system for identifying defects in a composite structure during fabrication thereof according to the present invention.

Embodiments of the system for identifying defects in a composite structure according to the present invention are generally referred to as numeral 10 in FIGS. 1 and 2. As shown in FIG. 1, the system 10 is positioned proximate a composite structure 22, which is generally comprised of a plurality of adjacent tows or strips 24 of composite tape. The strips 24 typically include a plurality of fibers embedded in a resin or other material that becomes tacky or flowable upon the application of heat. The strips 24 are arranged on a work surface, such as a table, mandrel, or other tool 26, and compacted with a compaction roller 20 to form the composite structure 22 according to an automated collation technique, which is known in the art. For example, an article entitled "Material Selection/Fabrication Issues for Thermal Plastic Fiber Placement" by Richard Sharp et al. published in the "Journal of Thermoplastic Composite Materials" (January 1995) discusses one conventional fiber placement process and is incorporated herein by reference. In addition, U.S. patent application Ser. No. 10/068,735, filed on Feb. 6, 2002, and entitled "Composite Material Collation Machine and Associated Method for High Rate Collation of Composite Materials," discusses another fiber placement process and is incorporated herein by reference.

In general, the system 10 comprises a camera 12 and a light source 14. The camera 12 and the light source 14 are positioned proximate the composite structure 22 in such a way that light reflecting off non-defective portions of the composite structure, and light that fails to reflect off of defects in the composite structure, or vice versa, creates visible images that can be captured by the camera 12. The camera 12 is connected to a processor for interpreting the images, or a storage device for storing the images, or both, as discussed more fully below. Details regarding systems and methods for identifying defects in a composite structure during fabrication thereof are included in U.S. patent application Ser. No. 09/819,922, filed on Mar. 28, 2001, and entitled "System and Method for Identifying defects in a Composite Structure," which is incorporated herein by reference.

As FIG. 1 illustrates, the camera 12 is positioned near the composite structure 22 so as to capture an image of a predetermined portion of the composite structure, typically immediately downstream of the nip point at which a composite tow is joined with the underlying structure. Alternatively, as FIG. 2 illustrates, a reflective surface 16 may be positioned near the composite structure (not shown in FIG. 2), and angled such that the reflective surface 16 reflects an image of a predetermined portion of the composite structure such as an image of that portion immediately downstream of the nip point at which a composite tow is joined with the underlying structure, i.e. immediately downstream of the compaction roller 20. In one embodiment of the present invention, the angle of the reflective surface 16 to the composite structure is 65°, but the reflective surface 16 may be positioned at any appropriate angle in order to reflect images of the illuminated portion of the composite structure to the camera 12. The camera 12 then may be positioned to point toward the reflective surface 16 in order to capture the close-range images of the predetermined portion of the composite structure from the reflective surface 16. More than one reflective surface 16 may be utilized in further embodiments of the present invention. The reflective surfaces 16 therefore cooperate in order to direct images of the illuminated portion of the composite structure to the camera 12.

For composite structures having curved/contoured surfaces, an image of the composite structure is advantageously captured from a position as close as possible to the nip point in order to obtain an accurate representation of the composite structure for processing. Thus, the configuration illustrated in FIG. 2 is particularly advantageous for capturing images of curved/contoured surfaces of the composite structure because the reflective surface 16 reflects an image of the composite structure for the camera 12 to capture from a position as close as possible to the composite structure. In addition, this configuration permits the camera 12 to be placed further from the composite structure than the reflective surface 16, such that the camera 12 does not obstruct the functionality of other parts of the fiber placement device, or vice versa.

The camera 12 can be a commercially-available camera capable of acquiring black and white images. For example, in one embodiment, the camera 12 is a television or other type of video camera having an image sensor (not shown) and a lens 13 through which light passes when the camera is in operation. Other types of cameras or image sensors can also be used, such as an infrared-sensitive camera, a visible light camera with infrared-pass filtration, a fiber optic camera, a coaxial camera, Charge Coupled Device (CCD), or Complementary Metal Oxide Sensor (CMOS). The camera 12 can be positioned proximate the composite structure 22 on a stand (not shown) or mounted to a frame 28 or similar device. In embodiments of the present invention that do not include a reflective surface, the camera 12 may be positioned approximately six inches from the surface of the composite structure 22, and mounted to the frame 28 by way of a bracket 30 and associated connectors 32. In embodiments of the present invention that do include a reflective surface, however, the reflective surface 16 may be positioned approximately three inches from the surface of the composite structure 22, and the camera 12, pointed toward the reflective surface 16, may be positioned further away from the composite structure, as described above. In further embodiments of present invention, the reflective surface 16 may be positioned at other distances from the surface of the composite structure 22, such as from one to six inches, to reflect an image of the surface of the composite structure that is as accurate as possible toward the camera 12.

The connectors 32 may be rivets, screws or the like that mount the camera 12 to the frame 28 in a stationary position. Alternatively, the connectors 32 may be a hinge-type connector that permits the camera 12, light source 14, and associated assembly to be rotated away from the composite structure 22. This embodiment is advantageous in situations where other parts of the fiber placement device, particularly the parts located behind the camera 12 and associated assembly, must be accessed, such as for maintenance, cleaning, or the like. FIG. 2 illustrates an alternative embodiment of the hinge-type connector 32 that mounts the camera 12, reflective surface 16, light source 14, and associated assembly (i.e. camera assembly) to the frame 28 by way of a bracket 30. The fastener 34, which may be a thumbscrew or any other fastener that may be removed or loosened with relative ease, may be tightened in order to secure the camera assembly in place for operation, then may be loosened or removed in order to rotate the camera assembly away from the compaction roller 20 and other parts of the fiber placement device.

In addition, a filter 15 can be placed on the lens 13 for filtering light in a particular manner. Specifically, the filter 15 is designed according to one embodiment to filter light such that only the infrared component or a certain infrared wavelength or wavelength(s) of the light can pass into the camera. Thus, the filter 15 prevents ambient visible light from entering the camera 12 and altering the appearance of the captured image. Other methods of filtering light can also be used to achieve the same result. For example, the camera may be designed to include a built-in filter of equivalent optical characteristics. In addition, the filter can be located between the camera lens 13 and image sensor. Alternatively, the camera may include an image sensor that is only sensitive in the infrared spectrum (i.e. an infrared-sensitive camera), thus eliminating the need for the filter.

The system 10 also includes a unique light source 14 that illuminates the composite structure 22 such that defects 36 on or in the surface of the composite structure 22 can be detected by the camera 12. The light source 14 may be positioned relative to the composite structure 22 such that the portion of the composite structure 22 where the camera 12, or the reflective surface 16 in the embodiment of FIG. 2, is pointed receives a sufficient amount of illumination from the light source 14 and, in some embodiments, the maximum amount of illumination, in order to highlight the defects 36, as discussed below. Further, the system 10 may include more than one light source. For example, the embodiment of FIG. 2 includes two light sources positioned relative to the composite structure and compaction roller 20 on either side of the reflective surface 16 and camera 12.

The light source 14 is adjustably positioned relative to the composite structure as described above by mounting or attaching the light source to a mounting apparatus 27, which as shown in FIG. 1, can include a main shaft 29, a secondary shaft 31, and a locking clamp 33 for quickly and accurately adjusting the position of the light source. The mounting apparatus 27, in turn, can be attached to the frame 28, to the camera 12, to the bracket 30, or to some other object that defines a common position for both the light source and the camera such that the light source and camera maintain a constant spatial relationship relative to one another.

A common problem in conventional machine vision systems is the inability to effectively illuminate and then to detect particular defects, such as dark flaws on a dark background. In particular, the quality and magnitude of the surface illumination of the composite structure is greatly affected by ambient lighting and by the reflectivity of the material. In order to effectively illuminate a dark flaw on a dark background, the system of one embodiment of the present invention advantageously employs an infrared light source. In this regard, the light source 14 can be selected from an infrared light or another type of light, such as an incandescent light or a halogen light, having an infrared component. In this regard, power levels in the range of about 5 W–25 W in the wavelength range of about 700 nm–100 nm are sufficient. In the embodiment shown in FIG. 1, the light source 14 may comprise a light emitting diode (LED), and in particular can include a plurality of LEDs arranged in an array or cluster formation. In one specific embodiment, the light source 14 includes 24 LED's mounted in an array upon a three-inch square printed circuit board. As a result of the infrared illumination, the LED array increases the contrast between the composite structure and a defect 36 relative to conventional systems. In another embodiment, the light source 14 includes an incandescent light fiber that emits light optically piped from a remote source (not shown) to an array or arrays of optical fiber sources.

In the embodiment illustrated in FIG. 2, dispersion elements 18 are located near the light source 14. The dispersion elements 18 break up and scatter the light emitted by the light source 14 such that areas of intense light created by the brightest portion of the light source 14 (i.e. hotspots) are substantially eliminated. The hotspots are undesirable because they prevent consistent illumination of the composite structure, which may cause errors in the processing of the images captured by the camera 14. The dispersion elements 18 are particularly advantageous for illuminating the curved/contoured surfaces of composite structures because the scattering of the light permits a larger portion of the composite structure to be illuminated. As such, more light illuminates the areas of the curve/contour that would not be effectuvely illuminated by conventional systems, such as the portions of the curve/contour that curve away from the light source 14.

Figure 3:
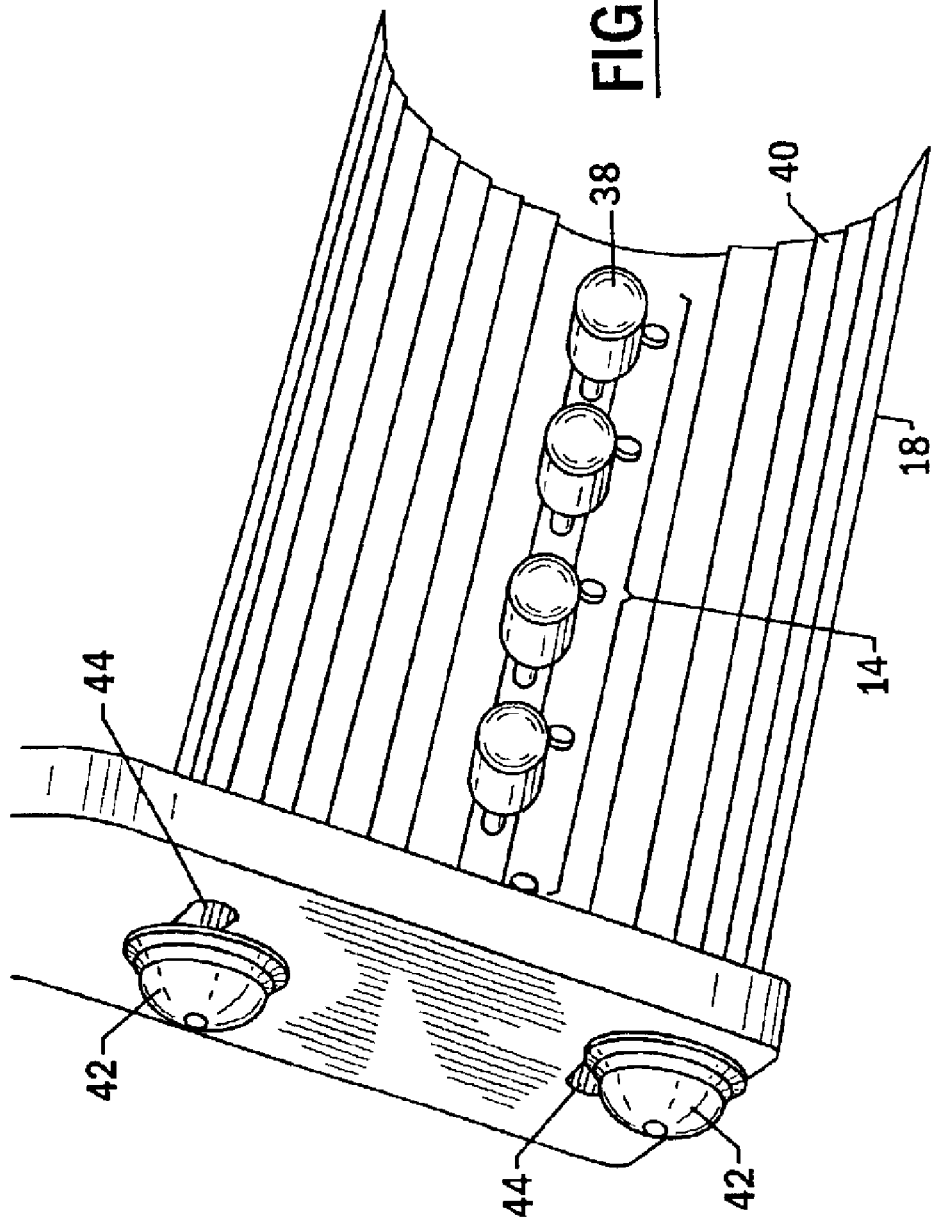
FIG. 3 is a detailed view of the light source according to the embodiment of the system for identifying defects in a composite structure as illustrated in FIG. 2.

FIG. 3 is an enlarged view of a light source 14 and dispersion element 18 according to the embodiment illustrated in FIG. 2. The light source 14 in this embodiment consists of four halogen light bulbs 38. The dispersion element 18 is advantageously located near the light source 14 and positioned in a way that directs the light emitted by the light source 14 toward the portion of the composite structure where the camera 12 or reflective surface 16 is directed. The dispersion element 18 may be curved toward the light source 14, such as in a parabolic shape, as shown in FIG. 3. On the surface of the dispersion element that faces the light source 40, the dispersion element may have steps 40. The steps 40 may be substantially parallel to the light source 14, and the distance between the steps 40 may be chosen to be sufficient to break up any hotspots that are incident on the dispersion element 18, such that the dispersion element 18 provides consistent illumination of the composite structure, which prevents errors in the processing of the images captured by the camera 14 due to inconsistent illumination of the composite structure. Alternatively, the shape and/or surface configuration of the dispersion element 18 may be modified in any way that produces consistent illumination and scattering of the light produced by the light source 14 over the desired portion of the composite structure.

In one embodiment, for example, the dispersion element has a parabolic shape with seventeen steps having a range of widths from 0.125 inches at the outer edge of the element to 0.250 inches at the center of the element and a uniform step height of 0.116 inches. In other embodiments, however, there may be different numbers of steps having different uniform or varying widths and different uniform or varying step heights. Furthermore, the dispersion element 18 may be adjusted in order to direct the light produced by the light source 14 and scattered by the dispersion element 18 toward the desired portion of the composite structure. For example, as shown in FIG. 3, the dispersion element 18 may be adjustably mounted to the mounting apparatus 27 with fasteners 42. The loosened fasteners 42 may move within slots 44 to correspondingly adjust the angle of the dispersion element 18 relative to the composite structure. Once the dispersion element is positioned appropriately, the fasteners 42 may be tightened to secure the dispersion element in the desired position. Adjustments of the dispersion element 18 may be enabled by any other method known to those skilled in the art, such as by electronic means that permit remote adjustment of the dispersion element 18.

It has been observed that the composite structure 22 produces high glare when illuminated across the direction of placement of strips 24, while producing substantially less glare when illuminated along the direction of placement of the strips. While conventional systems sought to eliminate the glare, the systems and methods of at least some of the embodiments of the present invention seek to exploit the glare. In particular, the systems and methods of these embodiments exploit the high-glare/low-glare phenomenon by casting light across the top layer of composite strips in a direction substantially perpendicular to the direction of placement of the strips, which produces a relatively large amount of glare on the top layer. The underlying layers, which produce significantly less glare than the top layer because of their orientation, will show through any gaps or other defects in the top layer and thus be easily located. In addition, twists and other surface defects in the top layer will alter the orientation of the strips in the top layer and thus correspondingly alter, i.e., decrease, the glare of the top layer at the defect location.

Further, while the high-glare/low-glare phenomenon occurs when illuminated with either visible light or infrared light, the filter 15 used in one embodiment of the system 10 substantially removes the glare caused by ambient light such that only the glare caused by the infrared light source is used to locate the defects 36. Accordingly, the filter 15 removes the interference of ambient light as the composite structure is examined for defects.

In any of the embodiments of the system for identifying defects in a composite structure described herein, there may be one or more cameras 12 and/or one or more light sources 14 with or without dispersion elements 18 (collectively referred to as light sources, hereinafter). In addition, the one or more cameras 12 and/or the one or more light sources may be moveable relative to the composite structure. The multiple cameras 12 and/or multiple light sources and the moveability of the camera(s) 12 and/or the light source(s) provides system 10 flexibility in order to capture the most accurate images of the composite structure. Multiple and/or movable light source(s) permit consistent and sufficient illumination of the desired portion of the composite structure, regardless of the shape of the composite structure. Likewise, multiple and/or moveable camera(s) 12 enable capturing an accurate image of any area of the composite structure, regardless of the shape of the composite structure. As such, the multiple and/or moveable light source(s) and/or camera(s) are particularly advantageous when illuminating and capturing images of and curved/contoured portions of composite structures. The multiple and/or moveable light source(s) and/or camera(s) are also advantageous in illuminating and capturing images of composite strips having a width that makes it difficult to illuminate and/or capture images of the entire strip, such that the position of the light source(s) and/or camera(s) may be moved over the entire strip, and/or multiple stationary light source(s) and/or camera(s) may be positioned to cover the entire strip.

Figure 4:
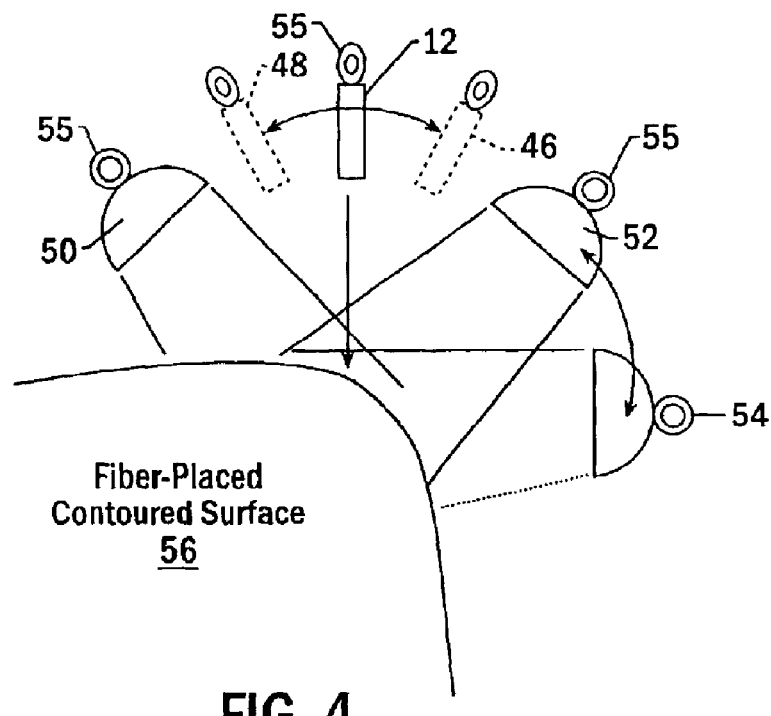
FIG. 4 is an alternative embodiment of a system for identifying defects in a composite structure according to the present invention that includes a moveable camera and stationary and moveable light sources.
Figure 5:
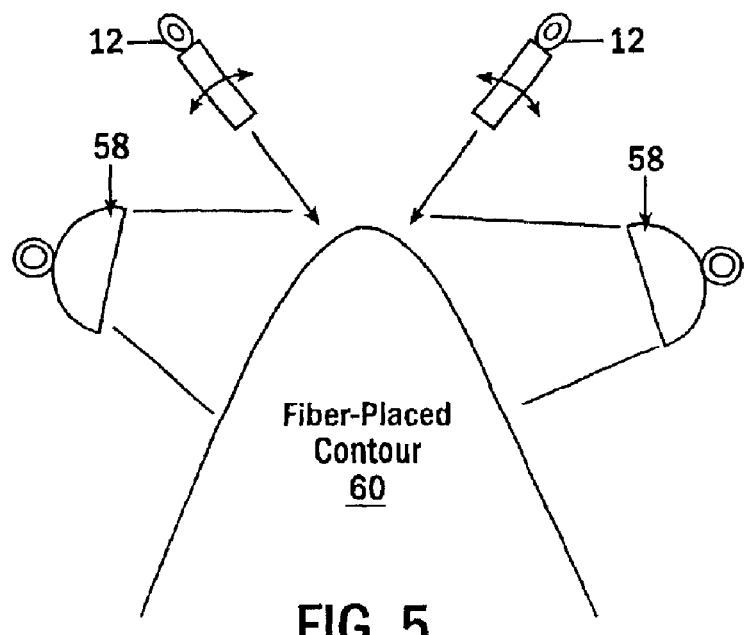
FIG. 5 is an alternative embodiment of a system for identifying defects in a composite structure according to the present invention that includes two moveable cameras and stationary light sources.

As FIGS. 4 and 5 illustrate, the system 10 may include any combination of moveable and/or stationary cameras and moveable or stationary light sources. In further embodiments, the reflective surface(s) 16 may be moveable and/or stationary. FIG. 4 illustrates a moveable camera 12, as represented by the alternate camera positions 46, 48. This embodiment also illustrates a stationary light source 50 and a moveable light source 52. The moveable light source 52 is capable of moving to alternate position 54 in order to fully illuminate the curve contoured portion of the composite structure 56. FIG. 5 illustrates an embodiment including two moveable cameras 12 and two stationary light sources 58 to obtain sufficient illumination and to capture accurate representations of the curved/contoured surface 60. Alternatively, one or both of the cameras 12 may be stationary and/or one or both of the light sources 58 may be moveable. The movement of the camera(s) and/or light source(s) and/or reflective surface(s) may be enabled by any means 55 known to those skilled in the art. For example, electrical or pneumatic servos may be attached to the camera(s) and/or light source(s) to control the movement. Examples of electrical or pneumatic servos include the PMA series servo systems commercially available from Pacific Scientific, the BMS N-series servo systems commercially available from Baldor Electric Company, and the Neometric and J-series servo systems commercially available from Compumotor, a division of the Parker Hannifin Corporation.

The system 10 of any of the embodiments described herein can also include a marking device 62 for indicating the location of the defects 36 on the composite structure 22, as shown in FIG. 1. The marking device 62, which in one embodiment is an inkjet marking system, may be attached to the frame 28 and is triggered by a processor 64 or similar device when a defect 36 that is to be reported to the operator is detected. In particular, the marking device 62 can spray a small spot of compatible ink of a highly visible color onto the surface of the composite structure 22 at the defect location to permit rapid access for repair and disposition. Other marking methods could also be used, such as audio or visual alerts and the like.

The automated collation process includes guiding the composite strips 24 from material creels (not shown) to an automated collation or fiber placement machine, which is known in the art. For example, such machines are made by Cincinnati-Milacron and Ingersoll Milling Machines. In particular, the composite strips 24 are guided to a head unit and fed under a compaction roller 20. Focused heat energy is then applied to the incoming material and the underlying material that was previously laid to adhere the two materials. With the combination of pressure and heat, the composite strip 24 is consolidated into the previous layer, thus forming an additional layer of the composite structure 22. Unfortunately, defects 36 may sometimes occur during the placement of the composite strip 24 onto the underlying composite structure 22. For example, in the case of fiber placement a gap may form between adjacent composite strips or a twist may occur in a composite strip during placement.

According to one embodiment of the present invention, as the head unit moves across the composite structure 22 and the composite strips 24 are laid down, the camera 12 and/or the reflective surface 16, which, along with the light source 14 and any dispersion element 18, can be mounted to the head unit, continuously captures images of the structure and the strips. If the composite structure 22 is not planar, the inspection point should be as close to the nip point as possible, as described hereinabove. If the composite structure 22 is planar, the inspection point can be located further from to the placement head unit. The images can be stored in a memory device 66 for future analysis and/or processed immediately by the processor 64, as discussed more fully below.

FIG. 6 shows an example of an unprocessed camera image 68 that comprises a plurality of pixels having a range from black through a plurality of shades of gray to white. In particular, the unprocessed camera image 68 illustrates a contrast between a potential defect, such as a gap between the composite strips 24, and the remaining portions of the composite structure 22 that are defect free. As shown in FIG. 6, potential defects are shown as black or gray areas 70, while the remaining portions of the composite structure 22 remain substantially white 72. However, the potential defects need further processing to determine if the potential defects are acceptable or unacceptable, as discussed below. In addition, only a predetermined area of the camera image is inspected in order to minimize interference.

The processor 64 receives the images 68 from the camera 12 or from the memory device 66 in which the images have first been stored. The processor 64 and memory device 66 can be components of a conventional computer, such as an IBM-style PC or Apple-based MAC. The processor 64 manipulates the images to facilitate the reliable detection of defects.

FIG. 7 shows a camera image 74, which is the same image as that depicted in FIG. 6 following binarization by the processor 64. In particular, all shades of gray above a predetermined threshold value have been changed to white, while all gray shades below the threshold have been changed to black to heighten the contrast of the defect 36 and improve the accuracy of detection. Advantageously, the system also includes a user interface 76 that is in communication with the processor 64. The user interface 76, such as a touch screen display driven by the processor 64, provides user controls 78 for adjustment of the binarization threshold. Generally, the setting of the binarization threshold involves a tradeoff between the sensitivity with which defects are detected and the resolution with which the defects are depicted. Typically, however, the binarization threshold is set to about 150 on a scale of 0 to 255. The interface 76 may also provide other controls, as discussed below.

Figure 8:
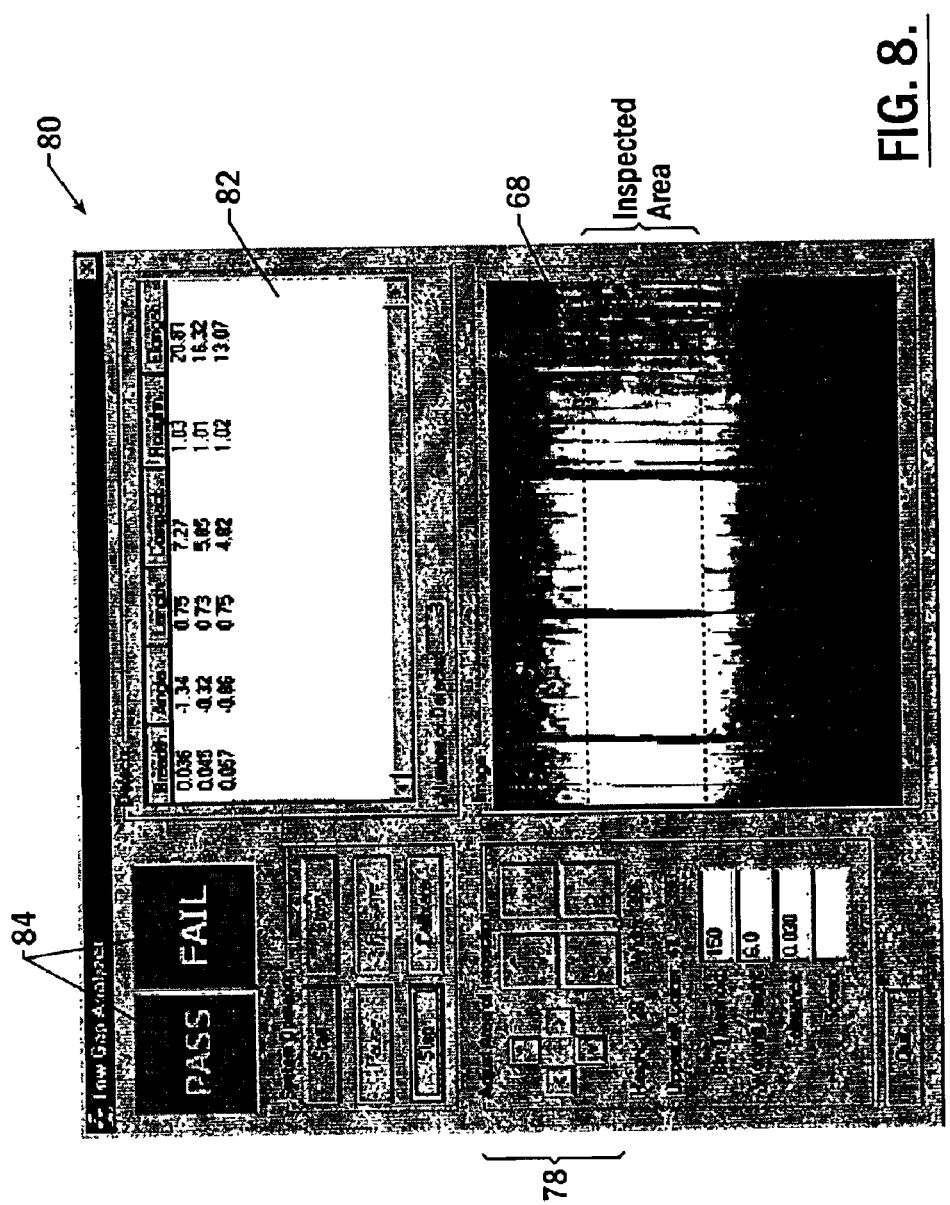
FIG. 8 is a view of a computer display and selected user controls according to one embodiment of the present invention.

FIG. 8 shows one embodiment of a portion of the user interface 76 according to the system 10 of the present invention. The user interface 76 can run from many software applications, such as Windows 98, Windows/NT, Windows 2000, Windows CE, Linux, Unix, and equivalents. The user interface 76 also includes a display screen 80, such as on a computer monitor, and can also include a keyboard and mouse (not shown) for permitting an operator to move a cursor about the display screen 80 and input the binarization threshold, the area of inspection, and the acceptable tolerances of the maximum allowed defect width, such as +/−0.030 inch of the detected defect 36. The display screen 80 could also be touch-sensitive for permitting the operator to input the desired settings by manually pressing regions of the display screen. As shown in FIG. 8, an image of the composite structure 22, which can be the unprocessed camera image 68 or the binarized camera image 74, is displayed for viewing by the operator. In addition to the displayed image of the composite structure 22, the display screen 80 also includes a defect table 82 which lists the discovered defects 36 and provides information for each defect, such as location, size, and the like. The display screen 80 can also include status indicators 84 that display whether a particular image area is acceptable or not acceptable based on predefined criteria, such as the tolerances discussed above.

Figure 9:
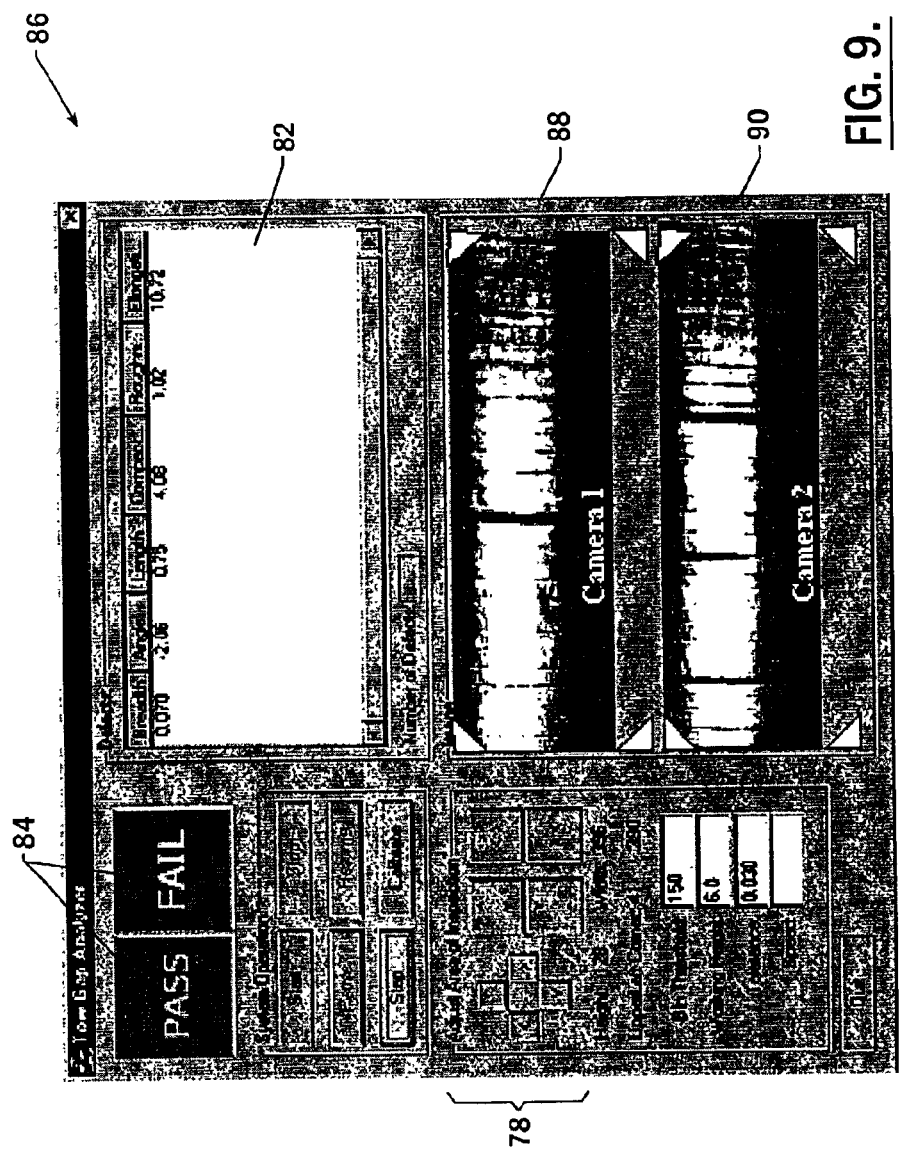
FIG. 9 is a view of a computer display and selected user controls according to an alternative embodiment of the present invention that includes two camera images.

FIG. 9 illustrates another portion of the user interface 76 according to the system 10 of the present invention when two cameras 12 are capturing images of the composite structure, as described above. In this embodiment of the user interface 76, a display screen 86 is included, similar to the display screen 80. As shown in FIG. 9, images of the composite structure 22, which can be the unprocessed camera image 68 or the binarized camera image 74, are displayed for viewing by the operator, illustrated by the camera images 88 and 90. In addition to the displayed images of the composite structure 22, the display screen 86 also includes a defect table 82 which lists the discovered defects 36 for each camera image and provides information for each defect, such as location, size, and the like. The display screen 86 can also include status indicators 84 that display whether the image areas are acceptable or not acceptable based on predefined criteria, such as the tolerances discussed above. Alternatively, to display the images of two cameras 12, two user interfaces as shown in FIG. 8 may be utilized with links therebetween, such that each interface displays an image from one camera and presents a link to the user interface that displays an image from the other camera. Furthermore, to display the images of multiple cameras 12, multiple user interfaces as shown in FIGS. 8 and/or 9 may be utilized with links therebetween, such that each interface displays images from one or more cameras and presents links to the user interface(s) that display images from the other cameras.

Thus, the present invention provides an improved system 10 for identifying defects 36 in a composite structure 22 by providing a light source 14 having an infrared component such that defects, and in particular defects that are oftentimes not detected by conventional systems, such as dark defects on a dark background and/or light defects on a light background, can be identified. In particular, the advantageous embodiments of the improved system 10 for identifying defects 36 in a composite structure provide a reflective surface 16, dispersion elements 18, and multiple and/or moveable light source(s) and/or camera(s) in order to ensure that the most accurate images of any area of the composite structure, even curved or contoured areas, are captured and processed. As a result, the system 10 of the present invention permits the operator to quickly identify and correct defects 36 which would otherwise create structural flaws or inconsistencies that may affect the integrity of the composite structure 22. As such, less material is wasted, less labor is expended in inspection, and less machine down time is incurred during the fabrication process; therefore, a lower cost composite structure is achieved on average.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for identifying defects in a composite structure during fabrication thereof, comprising:

a light source positioned relative to the composite structure for illuminating the composite structure, wherein light generated by said light source is reflected differently by defects in the composite structure than from portions of the composite structure that are defect free;

a dispersion element proximate said light source for scattering the light generated by said light source over the composite structure, wherein said dispersion element comprises a reflective surface having a stepped configuration to more evenly scatter the light over the composite structure;

a reflective surface proximate the composite structure and directed toward a portion of the composite structure that is illuminated; and a camera directed toward said reflective surface to receive images of that portion of the composite structure that is illuminated following reflection of the image from said reflective surface.

2. The system of claim 1, wherein said camera is positioned further from the illuminated portion of the composite structure than said reflective surface.

3. The system of claim 1, wherein said reflective surface is a mirror.

4. The system of claim 1, wherein said reflective surface comprises a plurality of reflective surfaces that cooperate to direct the images to the camera.

5. The system of claim 1, wherein said camera is an infrared-sensitive camera.

6. The system of claim 1, wherein said camera is a visible light camera with infrared-pass filtration.

7. The system of claim 1, wherein said light source is a halogen light.

8. The system of claim 1, wherein said camera is moveable relative to the composite structure.

9. The system of claim 1, wherein said camera comprises a plurality of cameras located at different respective positions relative to the composite structure.

10. The system of claim 1, wherein said light source is moveable relative to the composite structure.

11. The system of claim 1, wherein said light source comprises a plurality of light sources located at different respective positions relative to the composite structure.

12. The system of claim 1, further comprising a marking device for indicating the defects on the composite structure.

13. The system of claim 1, further comprising a processor for processing the images and outputting a response identifying a defect based upon the images.

14. The system of claim 1, wherein the composite structure comprises a plurality of composite strips, said composite strips being laid down by an automated collation process in which the composite strips are provided by a head unit and compacted to the underlying composite structure by a compaction roller, and wherein said reflective surface and said light source are proximate the compaction roller.

15. The system of claim 14, wherein said reflective surface and said light source are mounted on said head unit.

16. The system of claim 1 wherein the dispersion element comprises a plurality of steps extending parallel to said light source.

17. A system for identifying defects in a composite structure during fabrication thereof, comprising:
a light source positioned relative to the composite structure for illuminating the composite structure, wherein light generated by said light source is reflected differently by defects in the composite structure than from portions of the composite structure that are defect free;
a dispersion element proximate said light source for scattering the light generated by said light source over the composite structure, wherein said dispersion element comprises a reflective surface having a stepped configuration to more evenly scatter the light over the composite structure; and
a camera for receiving images of a portion of the composite structure that is illuminated.

18. The system of claim 17 wherein the dispersion element comprises a plurality of steps extending parallel to said light source.

19. A system for identifying defects in a composite structure during fabrication thereof, comprising:
a light source positioned relative to the composite structure for illuminating the composite structure, wherein light generated by said light source is reflected differently by defects in the composite structure than from portions of the composite structure that are defect free;
a dispersion element proximate said light source for scattering the light generated by said light source over the composite structure, wherein said dispersion element has a modified parabolic shape about said light source, and wherein said dispersion element has a stepped configuration arranged in a parabolic shape to more evenly scatter the light over the composite structure; and
a camera for receiving images of a portion of the composite structure that is illuminated.

20. The system of claim 19, wherein said dispersion element is at least partially curved toward said light source.

21. The system of claim 19, wherein said dispersion element is adjustable relative to the composite structure, such that said dispersion element scatters the light over a predetermined portion of the composite structure from which said camera receives images.

22. The system of claim 19, wherein said camera is an infrared-sensitive camera.

23. The system of claim 19, wherein said camera is a visible light camera with infrared-pass filtration.

24. The system of claim 19, wherein said light source is a halogen light.

25. The system of claim 19, wherein said camera is moveable relative to the composite structure.

26. The system of claim 19, wherein said camera comprises a plurality of cameras located at different respective positions relative to the composite structure.

27. The system of claim 19, wherein said light source is moveable relative to the composite structure.

28. The system of claim 19, wherein said light source comprises a plurality of light sources located at different respective positions relative to the composite structure.

29. The system of claim 19, further comprising a marking device for indicating the defects on the composite structure.

30. The system of claim 19, further comprising a processor for processing the images and outputting a response identifying a defect based upon the images.

31. The system of claim 19, wherein the composite structure comprises a plurality of composite strips, said composite strips being laid down by an automated collation process in which the composite strips are provided by a head unit and compacted to the underlying composite structure by a compaction roller, and wherein said camera and said light source are proximate the compaction roller.

32. The system of claim 31, wherein said camera, said light source and said dispersion element are mounted on said head unit.

33. A system for identifying defects in a composite structure during fabrication thereof, comprising:
a light source positioned relative to the composite structure for illuminating the composite structure, wherein light generated by said light source is reflected differently by defects in the composite structure than from portions of the composite structure that are defect free;
a camera for receiving images of a portion of the composite structure that is illuminated; and
a dispersion element proximate said light source for directing the light generated by said light source toward the composite structure, wherein said dispersion element has a stepped configuration to more evenly distribute the light over the composite structure.

34. The system of claim 33, wherein said camera is an infrared-sensitive camera.

35. The system of claim 33, wherein said camera is a visible light camera with infrared-pass filtration.

36. The system of claim 33, wherein said light source is a halogen light.

37. The system of claim 33, wherein said camera comprises a plurality of cameras located at different respective positions relative to the composite structure.

38. The system of claim 33, wherein said light source comprises a plurality of light sources located at different respective positions relative to the composite structure.

39. The system of claim 33, further comprising a marking device for indicating the defects on the composite structure.

40. The system of claim 33, further comprising a processor for processing the images and outputting a response identifying a defect based upon the images.

41. The system of claim 33, wherein the composite structure comprises a plurality of composite strips, said composite strips being laid down by an automated collation process in which the composite strips are provided by a head unit and compacted to the underlying composite structure by a compaction roller, and wherein said camera and said light source are proximate the compaction roller.

42. The system of claim 33 wherein the dispersion element comprises a plurality of steps extending parallel to said light source.

* * * * *